United States Patent [19]

Tammisalo et al.

[11] Patent Number: 4,683,581
[45] Date of Patent: * Jul. 28, 1987

[54] APPARATUS FOR X-RAY PHOTOGRAPHY OF THE AREA OF THE DENTITION AND OF THE JAWS

[75] Inventors: Erkki Tammisalo; Heikki Kanerva, both of Turku; Jaakko Aarnio, Helsinki; Markku Wederhorn, Espoo; Kai Laner, Helsinki, all of Finland

[73] Assignee: Orion-Yhtyma, Nilsiankatu, Finland

[*] Notice: The portion of the term of this patent subsequent to Feb. 24, 2004 has been disclaimed.

[21] Appl. No.: 696,776

[22] Filed: Jan. 31, 1985

[30] Foreign Application Priority Data

Feb. 1, 1984 [FI] Finland ................................. 840412

[51] Int. Cl.⁴ ............................................. A61B 6/14
[52] U.S. Cl. ...................................... 378/38; 378/197
[58] Field of Search ............................ 378/20, 38–40, 378/196–197; 74/422

[56] References Cited

U.S. PATENT DOCUMENTS

| | | | |
|---|---|---|---|
| 3,670,163 | 6/1972 | Lajus | 378/178 |
| 3,803,418 | 4/1974 | Holstrom | 378/177 |
| 4,241,254 | 12/1980 | Välilä | 378/40 |
| 4,541,293 | 9/1985 | Caugant et al. | 74/422 |

Primary Examiner—Craig E. Church
Assistant Examiner—John C. Freeman
Attorney, Agent, or Firm—Ladas & Parry

[57] ABSTRACT

An apparatus for panoramic X-ray photography of the area of the dentition and the jaws, comprising a frame part, a bearing part linearly movable in relation to the frame part, and a support arm attached rotatably to the bearing part, the arm having at one end an X-ray film and at the opposite end an X-ray source. The movements of the bearing part, the support arm and the film are synchronized in such a way that an image of an area of desired shape, e.g. the patient's dental arch, is obtained on the film. The invention provides a possibility, without shifting the patient, of altering the enlargement and, additionally of tilting the X-ray beam a desired angle in relation to the horizontal, whereby e.g. teeth oblique in relation to the vertical can be photographed more sharply. The support arm is attached to the bearing part through structural parts provided with guides extending in the longitudinal direction of the support arm, and with transfer means, so that the support arm, with the source of radiation and the X-ray film, can be transferred in a direction parallel to the X-ray beam. Furthermore, the said structural parts also have curved rails cooperating in order to effect tilting of the support arm. The movements are effected by stepping motors.

9 Claims, 2 Drawing Figures

APPARATUS FOR X-RAY PHOTOGRAPHY OF THE AREA OF THE DENTITION AND OF THE JAWS

BACKGROUND OF THE INVENTION

1. Field of the Invention

The present invention relates to an apparatus for X-ray photography of the area of the dentition and of the jaws, and of the type comprising a stationary frame part, a bearing part which is movably mounted to the frame part and preferably performs a linear movement, and a support arm which is rotatably attached using bearings to the bearing part and has at one end a source of X-radiation and at the opposite end a movable X-ray film, the movements of the bearing part, the support arm and the film being synchronized in such a way that a sharp image of only an area of the desired shape is obtained on the film, for example the area of the patient's dental arch.

2. Description of the Prior Art

In panoramic X-ray photography it is known, in order to obtain a sharp image of the dental arch, to allow the rotational axis of the support arm to move during the exposure in a predetermined manner linearly or non-linearly in such a way that this movement is dependent on the angular position of the support arm at each given time. The movement of the rotational axis may be linear, and parallel to the axis of symmetry of the dental arch, perpendicular to it, curved, or noncontinous between predetermined points. The enlargement can be adjusted by shifting the location of the patient, i.e. the head-supporting devices, in relation to the support arm. It is also known to change the patient's position so that the X-ray tube travels in relation to the patient either around the face or around the neck.

In practice the shifting and repositioning of the patient is always cumbersome and time-consuming. Furthermore, the known X-ray photography apparatus do not always provide so extensive possibilities for positioning and use as are generally desired in order to obtain a precise image of some specific area or part of an area.

SUMMARY OF THE INVENTION

Because of what has been stated above, it is an object of the present invention is to provide a general panoramic apparatus intended for X-ray photography of the dentition and the jaws, wherein the enlargement can be easily varied within the desired limits and the area of which a sharp image is obtained can be easily selected without shifting the patient.

In order to achieve this, the support arm is connected to the bearing part by mediation of structural parts which have been provided with guides extending in the longitudinal direction of the support arm, and with transfer means, in such a way that the support arm, and at the same time the source of radiation and the X-ray film, can be moved in relation to the rotational axis of the support arm and in a direction parallel to the plane of the X-ray beam. By means of this movement of the support arm in a direction parallel to the beam, i.e. the straight line connecting the source of radiation and the film, it is easy to select the enlargement ratio for the image. Furthermore, when the support arm is arranged to be able to make a complete rotation, the source of radiation can be allowed to travel either around the neck or the face of the patient without shifting the patient between these operations.

According to a further characteristic of the invention the support arm can, furthermore, be tilted in such a way that the straight line connecting the source of radiation and the film will no longer be on a horizontal plane. By means of such tilting it is possible to photograph sharply, for example, a patient's tooth which is at an angle to the vertical plane. It is evident that in such a case the reach of the beam is also preferably limited in the vertical direction in such a way that only the upper teeth or the lower teeth are photographed. When necessary, and according to the situation at each given time, the adjustments mentioned above can, of course, be carried out continuously also during the exposure. Especially today, when the use of a separate stepping motor for each adjustment is becoming established, the stepping motors being processor controlled-according to a predetermined program or predetermined programs, several mutually synchronized adjustments such as these are quite easy to implement.

DESCRIPTION OF THE PREFERRED EMBODIMENTS

Figure 1:
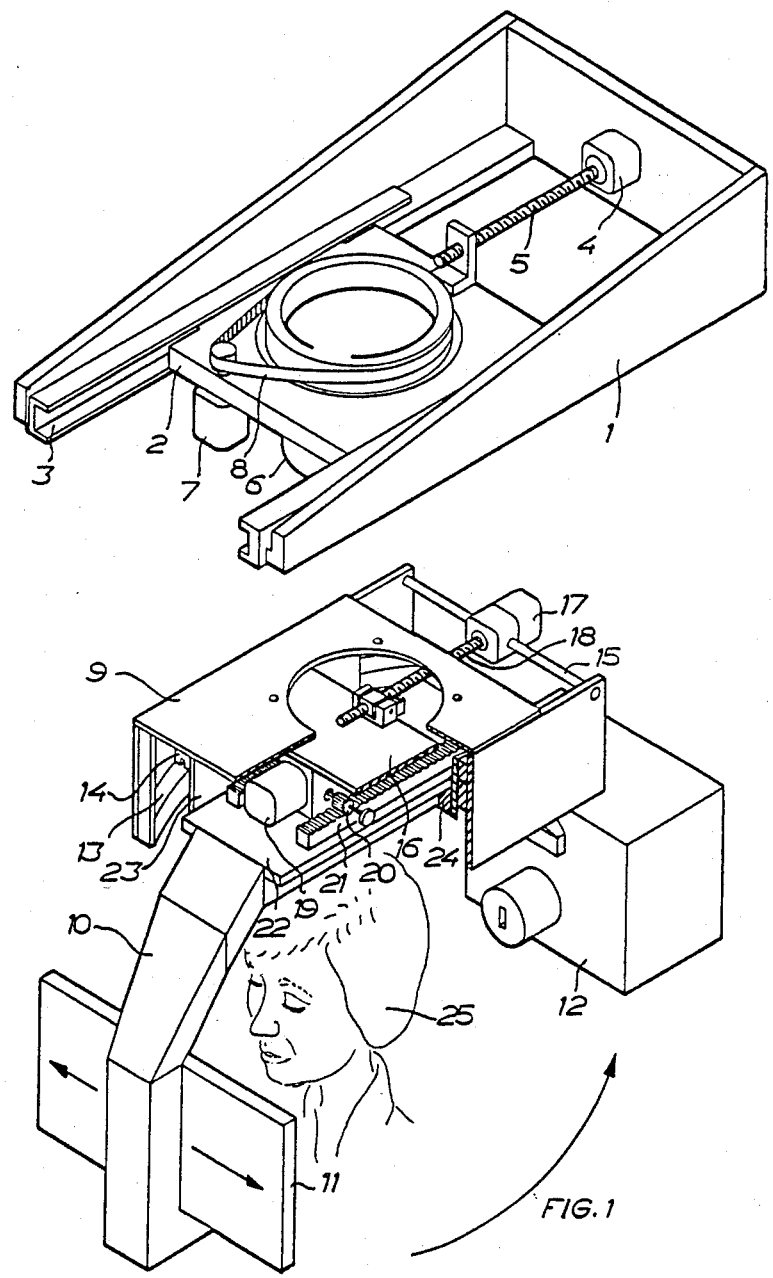
FIG. 1 depicts a perspective representation of one embodiment of the X-ray photography apparatus according to the invention, in part exploded for the sake of illustration.

The X-ray apparatus includes a stationary frame, which is indicated in the drawing by reference numeral 1 and which, in addition to the part shown in the drawing, normally includes a vertical pole attached to it and a stand resting on the floor. The protruding part 1 shown in the drawing is, of course, in practice encased, but for the sake of illustration this casing is not shown.

To the frame 1 there is attached using bearings a bearing part 2, which is capable of moving in the frame linearly along a horizontal plane and supported by rails 3. The movement is produced by a stepping motor 4, the shaft of which is a screw 5 which works in conjunction with the bearing part 2. To the bearing part 2 there is further attached rotatably with bearings a sleeve 6, which is rotated by another stepping motor 7 by transmission of a cogged belt 8.

To the sleeve 6 there is fastened by means of screws a casing-like part 9, which thus rotates together with the sleeve 6 and to which there is further attached with bearings in a manner depicted below a support arm 10, which constitutes an essential part of the photography apparatus.

At one end of the support arm there is a movable X-ray film 11 and at its opposite end a source 12 of X-radiation with means for limiting the beam. During the exposure the support arm 10 performs at least a partial rotational movement, the fulcrum moving at the same time linearly together with the bearing part 2, and the head of the patient being located between the source 12 of X-radiation and the X-ray film 11. This arrangement is already so familiar to experts in the art that it is not described here in greater detail. It is also evident that, as an alternative to the linear shift of the bearing part 2, it is possible to shift the patient, i.e. the chair of the patient, correspondingly during the rotational movement of the support arm.

It is an essential characteristic of the present invention that a possibility is provided for moving the support arm in the direction of the arm itself, in other words in a direction parallel to the straight line connecting the source of X-radiation and the film. In addition, a possibility is provided for tilting the support arm in such a way that the X-ray beam travels obliquely upwards or obliquely downwards. The latter adjustments are implemented as follows.

At the lower edge of the interior sides of the casing 9 there are provided curved guides 13, which work in conjunction with corresponding curved guides 14 in the control part 16. At the lower edge of the side piece 23 of the control part 16 there is additionally a strip 24, and the flat middle section 22 of the support arm 10 can move supported by this strip. The last-mentioned movement in a direction parallel to the X-ray beam is produced by a stepping motor 19, which rotates a transverse shaft and its cogwheels 20, the cogwheels for their part working in conjunction with cogged bars 21 in the middle section 22. Respectively, of course, it is possible to use friction wheels. The control part 16 for its part is moved by a screw 18 which grips it in an articulated way and serves as the shaft of the stepping motor 17, which for its part is articulated by means of a transverse shaft 15 to the casing part 9. The motor 17 thus affects the mutual shifting of the guides 13 and 14, and since the guides are curved, the transfer motor 17 of the control part 16 has been suspended in an articulated way.

The image enlargement coefficient can be changed by moving the support arm 10 in a direction parallel to the beam, in other words by means of the motor 19. By rotating the support arm 10 180° it is thus possible to allow the source of radiation to travel around either the neck or the face of the patient, and a suitable enlargement coefficient can be produced without shifting the patient.

For example, when somewhat slanted teeth are being photographed, it may be appropriate to tilt the support arm by means of the motor 17 and the curved rails 13, 14, at which time it is, of course, advisable also to limit the X-ray beam in the vertical direction in such a way that the teeth of only the upper jaw or the lower jaw are photographed. When using the arrangement according to the figure the tilting does not substantially alter the distance of the source of radiation, respectively the film, from the patient, which would occur if the tilting were produced by means of a horizontal transverse shaft.

Figure 2:
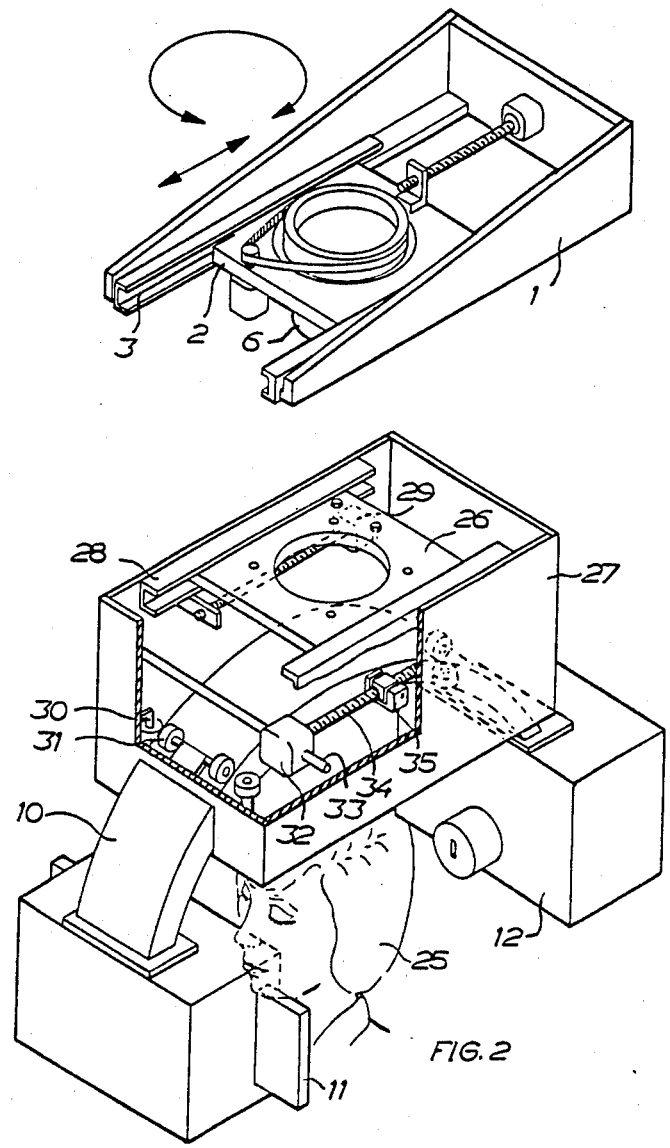
FIG. 2 depicts in a corresponding manner an alternative embodiment.

One alternative arrangement is shown in FIG. 2. In FIG. 2, there is a stationary frame as described previously and the linear transfer, i.e. the transfer in a direction parallel to the plane of the X-ray beam, is produced by means of a plate 26 attached to the sleeve 6, the edges of the plate being guided by rails 28 on the sides of the casing-like part 27. The transfer is effected by means of a motor 29, which is secured to the lower surface of the plate 26.

In this embodiment, at least the middle section of the support arm 10 is curved in such a way that the center point of the curve, i.e. the tilting axis, is again located approximately at the level of the head of the patient 25. Rollers 30, 31, attached by means of bearings inside the casing 27, work in conjunction with the arch 10, the rollers working against the side, upper and lower surfaces of the arch (the last-mentioned not shown), directing the arch along its own curved line. The transfer movement is produced by means of a spindle motor 32 attached turnably to the casing 27 by means of a shaft 33, the threaded shaft 34 of the motor engaging in a mating piece 35 attached turnably to the side of the arch.

As is well known by experts in the field, the film must also be moved synchronically with the rotational movement of the support arm. The shifting of the film is also produced preferably by means of a stepping motor, although this arrangement is not shown in the drawing. As was mentioned above, stepping motors are preferably controlled electronically in a manner known per se, especially by means of a programmed or a programmable microprocessor, in which case no mechanical means such as cams or the like are required for mutual synchronization of the movements of the different parts.

What we claim is:

1. An apparatus for X-ray photography of the area of dentition and the jaws, said apparatus comprising
   a stationary frame part; a bearing supported in the frame part and movable in relation thereto;
   a support arm mounted for rotational movement in relation to said bearing:
   a source of X-ray radiation provided at one end of the support arm;
   means for supporting and moving an X-ray film provided at the other end of the support arm;
   first means for rotating the support arm; second means for transferring the axis of rotation of the support arm along a predetermined path during the rotation;
   the movements of the support arm and the film being synchronized so that, during the movement, an image of the dental arch of a patient, is obtained on the film;
   bracket means for mounting the support arm in relation to the bearing part;
   guide means on said bracket means, said guide means extending in the longitudinal direction of the support arm;
   third means provided on said bracket means for transferring of the support arm in relation to its axis of rotation, together with the X-ray source and the X-ray film in a direction parallel to said longitudinal direction.

2. An apparatus according to claim 1, wherein said bracket means comprises, rail or the like, extending, as seen from above, in the longitudinal direction of the support arm, and a motor which exerts in the longitudinal direction of the rails by suitable driving members such as cogwheels.

3. An apparatus according to claim 1, wherein the support arm is attached to a rotating member, such as sleeve, in the bearing part, so as to allow the support arm to make a complete rotation in relation to the bearing part.

4. An apparatus according claim 1, wherein, for the taking of different photographs and enlargements, the initial position of the support arm is movable 180° around the patient, the required radial transfer of the support arm being performed at the same time.

5. An X-ray apparatus according to claim 1, wherein the bracket means between the bearing part (2) and the support arm (10) comprise means for adjusting the relative angle and tilting with respect to an axis which is perpendicular to the rotation axis of the support arm.

6. An X-ray photography apparatus according to claim 5, characterized in that the tilting means are made up of guides, such as curved rails, which are curved as seen from the side and work in conjunction with each other, the guides being parallel to the support arm (10) as seen from above.

7. An X-ray photography apparatus according to claim 2, characterized in that the rails (24) are provided in a control part (16), which as tiltable in relation to a casing part (9), the relative angle of tilting of the control part and casing part is with respect to an axis which is perpendicular to the rotation axis, attached with bearings rotatably to the bearing part (2).

8. An X-ray photography apparatus according to claim 2, characterized in that the rails (28) are arranged in a casing part (27), in relation to which the support arm (10) can be tilted, the relative angle of tilting of the control part and casing part is with respect to an axis which is perpendicular to the rotation axis, a plate (26) which moves supported by the rails being attached rotatably to the bearing part (2).

9. An apparatus according to claim 2, wherein the support arm is attached to a rotating member, such as sleeve, in the bearing part, so as to allow the support arm to make a complete rotation in relation to the bearing part.

* * * * *